US012636401B2

(12) United States Patent (10) Patent No.: US 12,636,401 B2
Rosenblatt (45) Date of Patent: May 26, 2026

(54) POLYMERIC IODOPHOR COMPOSITIONS AND METHODS OF USE

(71) Applicant: Solomon Rosenblatt, Philadelphia, PA (US)

(72) Inventor: Solomon Rosenblatt, Philadelphia, PA (US)

( * ) Notice: Subject to any disclaimer, the term of this patent is extended or adjusted under 35 U.S.C. 154(b) by 0 days.

(21) Appl. No.: 18/899,158

(22) Filed: Sep. 27, 2024

(65) Prior Publication Data

US 2025/0262343 A1 Aug. 21, 2025

Related U.S. Application Data

(60) Provisional application No. 63/630,645, filed on Feb. 21, 2024.

(51) Int. Cl.
| | |
|---|---|
| *A61L 15/18* | (2006.01) |
| *A61L 15/28* | (2006.01) |
| *A61L 15/44* | (2006.01) |

(52) U.S. Cl.
CPC ............... *A61L 15/18* (2013.01); *A61L 15/28* (2013.01); *A61L 15/44* (2013.01); *A61L 2300/106* (2013.01); *A61L 2300/404* (2013.01); *A61L 2300/418* (2013.01); *A61L 2400/04* (2013.01)

(58) Field of Classification Search
CPC ........... A61L 26/0023; A61L 2300/106; A01N 31/02; A01N 59/12; A01N 25/10
See application file for complete search history.

(56) References Cited

U.S. PATENT DOCUMENTS

| | | | | |
|---|---|---|---|---|
| 4,069,177 A | * | 1/1978 | Smith | ..................... A61L 15/60 |
| | | | | 525/54.32 |
| 4,095,595 A | * | 6/1978 | Stanford | ........... A61F 13/01034 |
| | | | | 602/76 |
| 2013/0316974 A1* | | 11/2013 | Wang | .................. A61L 26/0023 |
| | | | | 536/57 |

FOREIGN PATENT DOCUMENTS

| | | | | | |
|---|---|---|---|---|---|
| JP | 03141229 A | * | 6/1991 | | |
| WO | WO-8502422 A1 | * | 6/1985 | ............. | A61L 31/16 |
| WO | WO-2008117300 A2 | * | 10/2008 | ............. | A01N 59/12 |

OTHER PUBLICATIONS

Fan et al (Macromolecular Rapid Communications, Sep. 2022, doi: 10.1002/marc.202200203) (Year: 2022).*
Ito JP-03141229-A (Google English translation, downloaded Feb. 2025) (Year: 2025).*

* cited by examiner

*Primary Examiner* — Mark V Stevens
(74) *Attorney, Agent, or Firm* — IPath , PLC; Steven J. Miller

(57) ABSTRACT

Compositions comprising starch-acrylic polymers combined with elemental iodine are disclosed. The SAP-I compositions release non-toxic amounts of iodophor iodine in a sustained, controlled manner. Methods of formation and use of the compositions along with methods of creation and use of devices incorporating the compositions in a variety of healthcare and non-healthcare settings are set forth in detail herein.

16 Claims, 1 Drawing Sheet

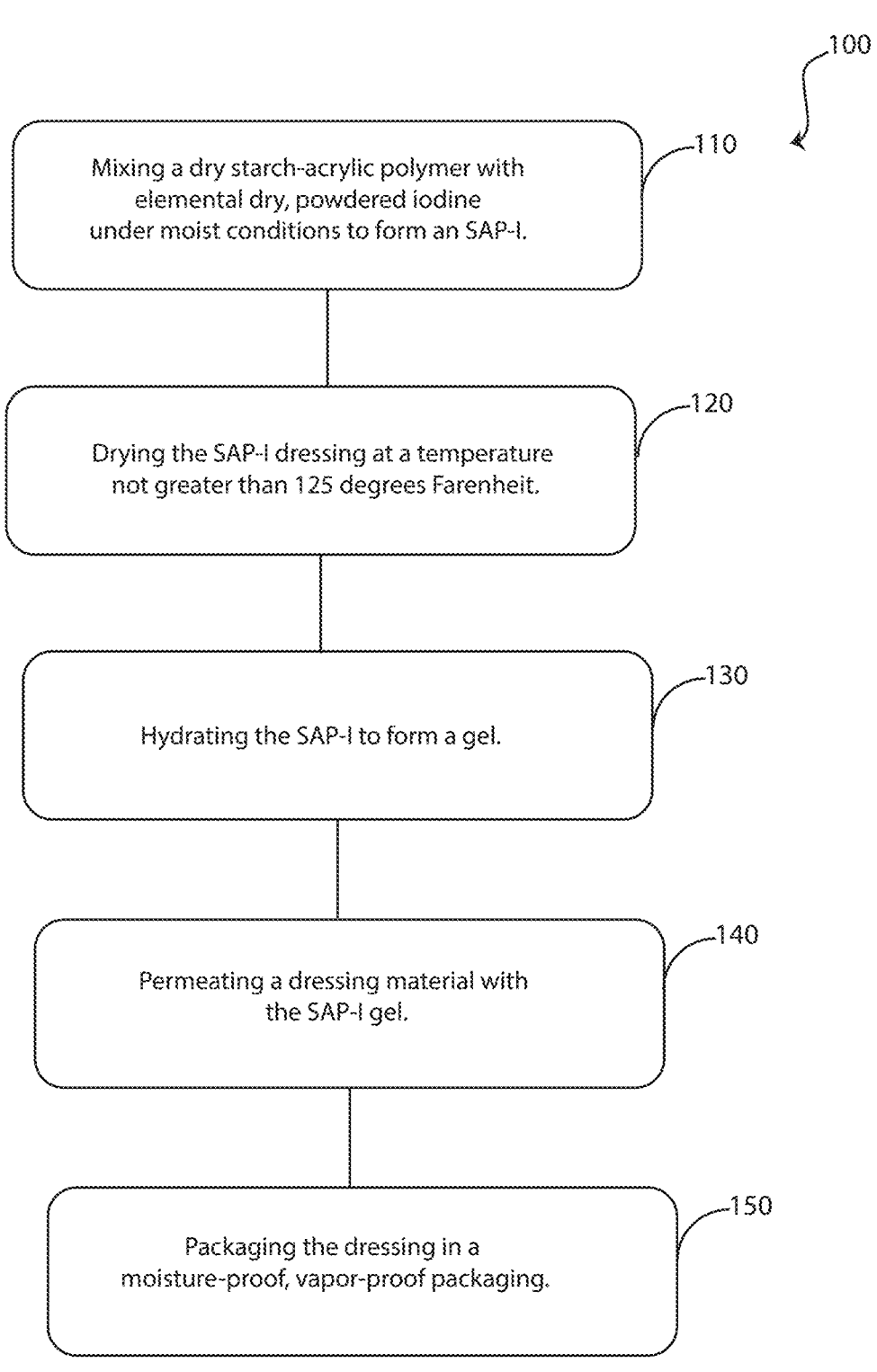

POLYMERIC IODOPHOR COMPOSITIONS AND METHODS OF USE

REFERENCE TO RELATED APPLICATIONS

This application claims priority of U.S. Provisional Application No. 63/630,645 entitled "Polymeric, Less Soluble, Broad Spectrum, Super-Absorbent Control Release, Antimicrobial Iodophor Materials" filed on 21 Feb. 2024, the disclosures of which are incorporated herein by reference in their entirety.

BACKGROUND

Technical Field

The disclosures herein relate to antimicrobial compositions. Specifically, the disclosed invention relates to super-absorbent polymeric iodophor compositions and dressings containing these compositions.

Background

Proper care of acute and chronic wounds is a widespread challenge for hospitals and patients. A retrospective analysis of Medicare data in the United States showed that in 2014, nearly 15% of Medicare beneficiaries (8.2 million people) suffered from at least one wound, including ischemic arterial ulcers, diabetic foot ulcers, pressure ulcers, and non-healing surgical wounds. The economic impact of wound care in this population was estimated to exceed $55 billion. This does not address patients and providers burdened with caring for acute and chronic wounds overseas, particularly in developing countries.

To reduce the length of time required to heal an open wound, optimal conditions for healing must be created. A wound should be kept clean to minimize microbial contamination. This includes physical washing and debridement and regular dressing changes to remove serous exudate and necrotic tissue—wherein bacteria colonize and grow, largely inaccessible to the patient's innate and acquired immune defenses. Wound fluid must be removed without increasing discomfort or drying out the wound. Mitigation of ongoing fluid and low-level blood loss is important to prevent development of anemia. Also, wound blood is a well-recognized adjuvant that encourages bacterial growth.

Existing antimicrobial compositions may be tissue toxic when contacting the wound bed, inhibiting re-epithelialization and wound closure. Existing dressing materials, such as cloth bandages, hydrogels, and other products absorb only a minimal amount of fluid and quickly become saturated, requiring frequent dressing changes that are labor-intensive and increase patient pain. Additional relevant background information is set forth in U.S. Pat. No. 5,071,648, the disclosures of which are incorporated by reference in their entirety herein.

Unmet needs for wound care to promote healing and reduce discomfort are infection control of the wound bed, exudate debridement, high fluid absorption, and hemostasis. Consequently, a convenient and effective means for providing a persistent concentration of a broad-spectrum antimicrobial composition with a highly absorbent, comfortable dressing is needed to advance wound care.

BRIEF SUMMARY

Various embodiments of compositions containing controlled-release forms of iodine whereupon topical iodine levels are sustained over long time periods are disclosed. Controlled sustained release of iodine is achieved by coupling elemental iodine, either directly or indirectly from any substance that contains elemental iodine, to starch acrylic polymers ("SAPs") comprising amylose. The compositions disclosed herein include a novel polymeric iodophor characterized by low water solubility yet having an extremely high absorptive capacity with the broad-spectrum antimicrobial properties associated with conventional iodophor and other iodine compositions. The high-absorption, controlled-release iodine compositions are incorporated into medical products, including wound dressings. The compositions are also suitable for biocidal use elsewhere within and outside of the healthcare industry. The polymeric iodine-containing compositions exhibit increased absorption of wound fluids over currently available products. Moreover, a color change indicates depletion of the iodine content signals the need for a dressing change. The polymeric iodine-release compositions can be formed as powders, poultices, sheets, gels, filters, coatings, impregnated foams, and other forms. Elemental iodine coupled to starch acrylic polymers results in antiseptic, broad-spectrum higher absorbency with controlled-release antimicrobial activity for wound care and biocidal products.

Disclosed is an antimicrobial composition comprising elemental iodine coupled with a starch acrylic polymer.

In some embodiments, the composition is formed as a powder. In some embodiments, the composition is formed as a flake. In some embodiments, the composition is formed as a gel. In some embodiments, the composition is formed as a sheet.

In some embodiments, the composition further comprises a hemostatic agent. In some embodiments, the composition further comprises further comprises a bulking agent.

In some embodiments, the elemental iodine complexes with the starch acrylic polymer as a non-ionic iodine molecule.

Disclosed is a wound dressing comprising an iodophor formed from elemental iodine and a starch acrylic polymer; and a bandage.

In some embodiments, the iodophor is a powder or a flake.

In some embodiments, the dressing is formed as a poultice. In some embodiments, the dressing is formed as a coated foam. In some embodiments, the iodophor is formed as a gel. In some embodiments, the iodophor is formed as a sheet.

In some embodiments, the dressing further comprises a hemostatic agent. In some embodiments, the bandage is an adhesive bandage. In some embodiments, the bandage is the bandage is a bandage roll.

Disclosed is a method of forming a wound dressing containing a polymeric iodophor composition comprising a mixing step, a drying step, a hydrating step, and a permeating step.

In some embodiments, the method further comprises a packaging step. In some embodiments, the packaging step comprises use of a moisture-proof, vapor-proof packaging.

The foregoing and other features and advantages of the invention will be apparent to those of ordinary skill in the art from the following more particular description of the invention and the accompanying drawings.

BRIEF DESCRIPTION OF THE DRAWINGS

FIG. 1 is an illustration depicting a method of forming a wound dressing containing a polymeric iodophor composition.

DETAILED DESCRIPTION

Various example embodiments of polymeric iodophor compositions and methods of use therefore are disclosed. These compositions are based on an amylose-containing acrylic polymer combined with elemental iodine. The amylose-iodine composition acts as an iodine reserve, incorporating large amounts of elemental iodine but control-releasing, non-toxic amounts of iodine from an iodophor into the wound over a long time period. The absorptive starch carrier is also non-toxic and safe as manifest by the use of saponified starch or starch-like acrylic polymer gels as a pharmaceutical diluent and as viscous inert carriers for in sustained drug delivery compositions. The amylose-acrylic starch acts as a super-absorbent starch polymer ("SAP") that pulls exudate from the wound surface, holding over eighty times its dry weight in water. Moreover, the amylose-iodine binding starch-acrylic polymer compositions can be incorporated into topical gels, ointment, sponges, powders, poultices, and other materials. Consequently, the compositions and substrates disclosed herein simultaneously address multiple requirements for wound healing, namely infection control by reducing or eliminating bacterial colonization of the wound bed and exudate, wound fluid control by absorbing large amounts of exudate where present, debridement by adsorbing fibrin, cellular debris, and other non-fluid exudative material, applying low-grade hemostatic pressure to the wound bed, and reducing patient discomfort by application of a soft, shock-absorbing protecting, semi-occlusive material that conforms to the wound surface.

Definitions

Certain terms should be afforded their broadest reasonable meaning as interpreted by a person of skill in the art. For example, "optionally" is intended to introduce a non-limiting example. The phrases "in one embodiment" and "in some embodiments" do not necessarily refer to the same embodiment(s), although they may. Furthermore, the phrases "in another embodiment" and "in some other embodiments," as used herein, do not necessarily refer to a different embodiments, although they may. The various example embodiments as described herein may be readily combined without departing from the scope or spirit of the disclosed inventions. The term "or," unless otherwise specified, is inclusive and is equivalent to "and/or." The term "based on" is not exclusive and allows for use based on additional factors not described unless the context clearly dictates otherwise. Throughout the written description, the meaning of "a," "an," and "the" include plural references. The meaning of "ion" includes "in" and "on." The terms "comprises" and "comprising," as used herein, specify that certain features are present in the described embodiment(s), however this phrase should not be interpreted to preclude the presence or addition of additional step, operations, features, components, and/or groups thereof.

The several example embodiments disclosed herein are written for use in a healthcare setting, however this is not meant to be limiting. In some embodiments, other uses are employed.

As used herein, "upper" refers to a direction away from or further from a more central part. For example, away from the body and toward the outer, more superficial surface of a wound or a dressing.

As used herein, "lower" refers to a direction toward a more central part. For example, closer to the body and toward the more central, deeper aspects of a wound or a dressing, away from the surface or the wound or the body.

Any directional references as used herein, such as right, left, up, down, top, bottom, and the like are intended for convenience of description and do not limit the disclosed structures to any particular positional or spatial orientation.

As used herein, "povidone" means polyvinylpyrrolidone.

As used herein, "iodophor" means a composition containing elemental iodine and a material that affects the release of iodine from the composition, generally slowing the release of iodine. An iodine-containing composition that provides controlled-release iodine, for example, is an iodophor as used herein. A prominent example of an iodophor from the prior art is polyvinylpyrrolidone-I, i.e., "povidone iodine" or "PVP-I." Iodophors release iodine gradually in a sustained-release manner. Iodine and, consequently, iodophors, are bactericidal and viricidal in relatively small concentrations.

As used herein, "compound" means a combination of substances bound together by covalent bonds or ionic bonds. Substances may refer to molecules or individual atoms.

As used herein, "complex" means a combination of substances held together by forces weaker than an ionic bond, such as hydrogen bonds and Van der Waals forces, for example. Complex is used interchangeably with "adduct." Other forms of "complex" and "adduct," whether used as a noun or a verb (including past-tense, participle, and gerund forms) are similarly used interchangeably.

With the foregoing background, summary, and definitions in mind, what follows is a detailed discussion disclosing various example embodiments.

Composition and Polymers

Iodine rapidly penetrates through bacterial and fungal cell walls, and viral envelopes, resulting in oxidation of proteins, fatty acids, and nucleic acids, ultimately leading to cell death. Iodine is an extremely broad-spectrum antimicrobial.

Prior art compositions configured to provide sustained release of elemental iodine, such as povidone iodine and polyvinyl alcohol foam-iodine complex ("PVA-I"), have significant deficiencies. Direct application of povidone iodine solution results in high concentrations of free iodine in an open wound. This results in tissue toxicity that is inhibitory to wound healing. Absorption of high levels of free elemental iodine released from povidone-iodine in a non-epithelialized wound bed have also generated systemic iodine toxicity, including renal failure and metabolic acidosis, and is therefore contraindicated.

As described in U.S. Pat. No. 5,071,448, the use of a controlled release iodophor PVA-I as a wound antimicrobial results in much lower free iodine levels, thus mitigating systemic toxicity. Regardless, however, PVA-I is relatively non-absorbing and can be rapidly overcome with volumes of serous exudate present in many wounds. Moreover, integration of dry PVA-I into dressings creates a stiff, noncompliant material which, therefore, must be applied in a pre-moistened state to conform to the wound bed and must remain moist to maintain functionality. Iodine content of a PVA-I dressing sheets are chemically limited to about 6%-8% by weight of the polymer sheet, requiring more frequent dressing changes to maintain adequate wound concentrations of iodine. Additionally, absorbency is limited by the high-density PVA sponge material and is further reduced by the requirement to pre-moisten the dressing.

In contrast to prior art starch-iodine polymer compositions, the association between starch and iodine combined in a starch acrylic polymer does not require the presence of iodine ions but occurs with non-ionized elemental iodine. To compound with the starch (amylose) of a starch-acrylic polymer, a linear Tri-iodide, $I^3$ molecule must form, followed by incorporation into an α-helix configuration of the starch (amylose) molecule. The $I^3$-amylose association creates the characteristic blue-black color seen when testing for starch, such as with Lugol's solution. Without the presence of the iodide ion, (e.g., provided as $K^+$ $I^-$), elemental iodine—$I^2$, compounding of iodine into $I^3$ cannot take place:

$$I^2 + I^- = I^3$$

$I^3$ – starch complex yields blue–black color

Neither iodine nor iodide ions alone will complex with amylose. Therefore, the reaction between elemental iodine alone and the starch part of the grafted polymeric superabsorber must not be an iodine-polymer compound because no iodide is used in forming the combination. The combination may instead be through a weaker, non-ionic attraction, such as by hydrogen bonds or Van der Waals forces. Electric charges surrounding the amylose starch backbone cause an attraction and attachment to elemental iodine. Compounds and complexes of starch with iodine both generate a blue-black color, although by different mechanisms.

Amylose-based controlled release iodine-containing acrylic polymers are incorporated into wound healing dressing platforms, e.g., powders, poultices, coated foams, sheets and gels, and others. Amylose is a non-toxic and renewable starch polysaccharide comprising α-helical chains of (1-4)-D-glucose monomers. Although amylose may exist as an amorphous aggregate of polysaccharide chains, pairs of chains may self-aggregate to form a left-handed a helix. Many forms of the amylose a helix exist and are denoted "V-form" based on the number of glucose molecules forming one complete turn or the helix. Notably, the α-helix forms a complex, when mixed with elemental iodine under conditions described herein. Individual iodine molecules are incorporated into the hydrophobic center of a 2-chain helix wherein iodine becomes a "guest molecule" within the amylose "host molecule" helix. The amylose-iodine addition is hydrophilic. This results in aqueous reactivity of the amylose-iodine addition while adding possible large amounts of iodine, which is relatively hydrophobic but still very minimally water soluble. The iodine is slowly solubilized in the polymer and released by the resulting iodophor at a sustained, gradual rate as conditions in the wound (acid pH, microbial amylases, e.g.) gradually hydrolyze the amylose chains, progressively releasing iodine over time.

Amylose may be used as a thickener, a water binder, an emulsion stabilizer, and a gelling agent. Amylose chains have a hydrophobic interior that can bind to hydrophobic molecules, including iodine. Various properties of an iodophor composition, such as firmness, viscosity, and absorptive capacity, are adjusted by changing the amylose concentration and cross linking of the acrylic portion of the polymer, in some embodiments.

Iodine has an affinity for various components of starch, particularly amylose. When combined with amylose, certain Iodine species (i.e., $I_3$, $I_5$, $I_7$, e.g.) reflect light in a narrow wavelength range, creating a deep blue-black color. Pectin, amylopectin, cellulose, and other polysaccharide molecules do not necessarily combine with iodine to create species that reflect only blue light. The intensity of the color is proportional to the relative concentrations of iodine and the amylose composition of the starch. In contrast, non-complexed, elemental iodine, whether free or in an aqueous solution with potassium iodide, presents a reddish-brown color. The amylose-iodine combination gradually releases a blue iodophor-derived iodine into the wound in non-toxic concentrations that nonetheless remain bactericidal and fungicidal.

Amylose in a wound is gradually consumed through hydrolysis and reaction with exudates requiring dressing changes. Iodine is lost through absorption, oxidation reactions with proteins, and vaporization. As amylose is consumed, the number of iodine binding sites decreases, releasing more iodine, and the color of a dressing incorporating amylose-iodine combination gradually changes first from deep blue-black and then to gray/white as the insoluble iodophor is depleted of its iodine. Consequently, the observed color change of a wound-care starch acrylic polymer material incorporating the amylose-iodine complex, initially being black and then turning color, can be used as a visual indicator that readily and unambiguously reflects over time the depletion of the antimicrobial effect of the material, signaling dressing change is needed.

Starch acrylic polymers ("SAPs") are a known class of insoluble biodegradable polymeric materials that uniquely have an extraordinary capacity to absorb water and aqueous-based fluids. When flakes of an SAP are contacted with a water-based fluid, they absorb large volumes of the fluid, swelling to many times their dry dimensions into a granular slurry. The resulting material has a gel-consistency and containing particulates. SAPs may absorb about 180 times their weight in water. SAPs are commercially available from various manufacturers. Although extremely absorptive, SAPs do not complex with nor otherwise retain or mix well with elemental iodine and are difficult to combine, as they are both insoluble powders in water. Like iodine, SAP polymers are largely insoluble in water and even less soluble in dilute aqueous iodine solutions. Disadvantageously, viscous swelling of SAPs in water prevents mixing necessary for reaction conditions with iodine. Additionally, salts occupying reactive sites within the SAP polymers results in reduced water absorption and reduced amylose-iodine binding capacity.

To overcome the difficulty in combining iodine with these super-absorbent SAPs, it was conceived that if elemental iodine could be adducted to the starch (amylose) portion of SAP polymers, a super-absorbent composition having broad-spectrum antimicrobial activity would result, and when formed into an appropriate useful state it can be incorporated into wound-care dressing materials, making superior absorbing wound dressings.

Hereinafter, "SAP-I" refers to a starch-acrylic polymer wherein elemental iodine is coupled with the amylose starch component of the SAP. To form the SAP-I, solid-state reaction conditions were created by directly mixing elemental dry powdered iodine with dry SAP polymers, but under moist conditions, in some embodiments. Iodine is soluble in water at room temperature to about 1 gram in 3,250 milliliters ("mL") of water. For iodine to react it must be solubilized. The iodine is slowly solubilized in a limited moist, warm, closed environment with high mechanical sheer mixing, is vaporized and dissolves up to iodine's slight solubility in water and reacts accordingly. Thereafter, ambient moisture levels are precisely monitored to prevent the premature swelling of the SAP before reacting with the iodine in order to maximize combining of iodine with the SAP.

SAP-I has about half the water absorptive capacity of non-SAPs, although this lower absorption is still far higher than most currently available compositions used in wound dressings and leverages the broad-spectrum antimicrobial activity of iodine to promote wound healing. In some embodiments, SAP-I is dried and provided as flakes or a granular powder having a deep, bluish black color.

In some embodiments, SAP-I is combined with an alkaline metal carboxylate salt of a starch-polyacrylonitrile graft copolymer (e.g., Water Lock®, a product of the Grain Processing Corporation, Muscatine, IA).

A comparison of the water-absorptive capacities of several iodophor compositions compared to SAP-I is presented in Table I below.

TABLE I

| MATERIAL | IODINE CONTENT | LIQUID PICKUP (multiple by weight) |
|---|---|---|
| Moist packaged PVA-I sponge | 6% | >3x |
| Dry PVA-I sheet | 6%-8% | 6x |
| Cadexomer | 0.9% | <3x |
| SAP-I dry flakes as a poultice | 20% | >40x |

Another example of a starch-grafted, less soluble polyacrylate is Sanwet IM-1000 (Sanyo Chemical, Kyoto, Japan) and its series that can be used to produce powders. IM 1000 MPS polymers are also part of this series and are also capable of combining with iodine but are more water soluble, thus having improved gel-forming characteristics required for creating spreadable gels or coatings. The series differs in the degree of chain cross-linking, resulting in varying physical properties.

These super-absorbent polyacrylic starch grafts commonly have starch backbones that combine with iodine to form a starch-iodine-polymeric composition that resembles a complex; however, this iodophor is formed by a different reaction than complexing and is instead an adduct-type of addition.

In every embodiment described herein, iodine is hybridized with a starch polyacrylate compound by mixing elemental iodine and SAP in the presence of water to produce a damp "curd" that is nearly black in color. The material is then dried, ground, and passed through a sieve. This produces the dry SAP-I powders having various particle sizes depending on the sieve used. High shear processing conditions and control of available moisture are necessary whereby relatively insoluble elemental iodine is taken up by the amylose molecules in a complex with the polyacrylonitrile. Despite iodine's minimum insolubility in water, it is rapidly taken up by the amylose-SAP composition in the presence of moisture. The dry mixture is initially an orange-tan color but turns to deep blue-black upon uptake of iodine by the amylose.

In some embodiments, the SAP-I comprises about 20 percent iodine by weight. In some embodiments, the SAP-I comprises between about 1.5 percent and about 20 percent iodine by weight. In some embodiments, the SAP-I comprises between about 10 percent and about 15 percent iodine by weight. In some embodiments, the SAP-I comprises between about 20 percent and about 25 percent iodine by weight. In some embodiments, the SAP-I comprises less than about 15 percent iodine by weight. In some embodiments, the SAP-I comprises greater than about 25 percent iodine by weight.

The fully complexed SAP-I composition is then dried, ground, and sieved, in some embodiments, to form particles within a defined size range for making wound gels, poultices, other dressing materials, and sanitizing materials and devices.

SAP is thought to absorb water through the reaction of hydrophilic groups with individual water molecules. In an SAP-I wound-care composition, many of the hydrophilic groups bind to elemental iodine guest molecules and are not available to bind with water. Regardless, we have found that SAP-I compositions still have sufficient binding capacity to exceed water absorption capacity (by weight) of currently available absorbent dressings. In an SAP, the degree of saponification of nitrile carboxylate groups on the acrylic polymer governs properties of various SAPs producing suitable forms for making insoluble antimicrobial components for various types of would care dressings, wound packing material, and incorporation into sanitizing and/or drug delivery devices.

Final properties of the composition depend on many factors. Examples are the degree of saponification of starch acrylonitrile graft polymers, cross-linked starches, grafted sodium polyacrylates, similar starch co-polymers, and their combinations. The range of water absorbing capability is dependent on the degree of cross-linking and iodine trapping by a mechanism theoretically similar to the starch iodine reaction, the type of starch incorporated with the SAP, and overall iodine content. For example, in some embodiments, the SAP forms highly hydrated, granular gels. In some embodiments, the SAP forms a low viscosity, creamy gel, depending on the degree of cross-linking between starch and polyacrylate chains. It was anticipated that elemental iodine addition would make the SAP compositions much less absorbent. Because amylose uniquely retains elemental iodine within the amylose helical structure, in theory, the incorporated iodine occupies hydrophilic binding sites in the starch lattice otherwise available to bind with water. Surprisingly, however, some SAP-I materials still form highly absorbent polymers even with the much less soluble SAP-I powders, creating a particulated gel composition.

Examples of excipients that may be combined with SAP-I in an iodophor wound care composition e.g., poultice, include bulking agents such as inert cellulose powder, polyethylene fine flakes; and/or beneficial agents e.g., hemostatic agents such as styptics containing aluminum salts such as aluminum sulfate, and other healing drugs in powder form. Varying the amount of bulking agent, such as a crystalline cellulose, distributes the SAP-I composition content to more uniformly spread within the poultice.

SAP-I gels are tailored to a desired viscosity for different applications, e.g., by water content and by variation of the amylose-polyacrylate ratio in the polymer which can also modulate the rate of release. Variation of the proportion making up the starch to polyacrylate in the iodine adducted polymer may also be used to modulate the rate of release of free iodine or pharmaceutical compounds similar to the mechanism described in U.S. Pat. No. 4,713,237, the disclosures of which are incorporated herein by reference.

Substrates and Dressings

Prior art wound dressings incorporating iodophor compositions have many limitations. For example, iodine may be complexed with insolubilized polyvinyl alcohol (PVA) and formed into dense, open-celled sponge sheets. These low-solubility iodophor-based PVA sponge dressings are chemically based on hydroxylated polyvinyl acetyl alcohol foam that is subsequently complexed with iodine. The iodophor complex releases iodine in a sustained and controlled manner in microbicidal concentrations that are not toxic to healthy tissue. Incorporating borate into the PVA foam sheets further broadens effectiveness. Disadvantages of the PVA foam include a need to maintain dampness of the dressing, which is stiff and noncompliant when dry. A soft, compliant dressing surface is necessary to conform to the wound bed to provide increased patient comfort and uniform delivery of iodine to all wound surfaces. Application of a PVA-I dressing, which must initially be pre-moistened, reduces the fluid absorptive capacity of the dressing. The dense PVA foam structure is incompatible for incorporation with other compositions which may be desirable in treating a particular wound, such as hemostatic agents or proteolytic enzymes that may be used to dissolve a dense fibrinous exudate. Furthermore, the polymer synthesis and manufacture of PVA-I is expensive. The process involves volatile toxic materials, e.g., formaldehyde to make the foam, requiring extensive pollution mitigation measures to contain iodine vapor. Finally, PVA polymers are not biodegradable, which may increase disposal costs.

A second example of an iodophor composition is marketed by Smith & Nephew (Smith & Nephew, Inc., Memphis, Tennessee) and branded as "Iodosorb." Iodosorb is an ointment comprising an iodine-reacted starch cadexomer formed into absorbent beads. Upon hydration with wound exudate, the beads deliver controlled-release iodine. Chemically, the iodophor composition is based on a low molecular weight dextrin reacted with epichlorohydrin coupled with an ion exchange group in a glycol base. The product is only available in a squeezable tube or as an ointment-impregnated gauze. Iodosorb has an iodine content-less than 1% by weight—and its exudate absorbency is extremely limited, resulting in the need for more frequent dressing changes.

The new dressing strategies disclosed herein incorporating the starch acrylic polymer-iodine complex (SAP-I) overcome these deficiencies. SAP-I powders can be manufactured with different iodine concentrations. SAP-I powders swell to greater than 80 times their weight when hydrated, resulting in substantially improved fluid absorbing capacity compared to polyvinyl alcohol/iodophor sponges and cadexomer ointments. SAPI-I compositions exert antimicrobial action both to the tissue of the wound bed and importantly to retained exudate. SAP-I is incorporated into various materials to create comfortable, non-adherent dressings. In some embodiments, the dressings are configured as flexible, porous hydrophilic pouches, bags, or poultice made of porous nonwoven restraining cloth containing the SAP-I flakes or powder. The SAP-I expands substantially with absorption of serous exudate from the wound from multiple mechanisms by hydration of the hydrophilic SAP-I composition and capillary action drawing fluid into interparticle voids throughout the SAP-I composition. Encasement of the SAP-I within a bag fabricated from small-pore heat-sealing and wicking non-wovens, such as teabag fabrics, develop non-adherent gel surfaces that do not stick to the wound bed and can be easily removed and changed without causing pain or tissue trauma.

In some embodiments, an absorbent paper product cloth, foam or other pressed, non-woven material is impregnated with a gel suspension of SAP-I, pressed into and dried, cut to size, and packaged as a wound dressing. In some embodiments, a woven cloth product such as a gauze or other sheet substrate, is impregnated with a gel suspension of SAP-I, dried, and is formed as a rolled wound dressing. In some embodiments, an aqueous suspension of SAP-I, is pressed into an absorbent sheet, dried, and packaged as a wound dressing.

In some embodiments, a paper product or other pressed, non-woven bandage material is impregnated with a partially hydrated, semi-solid (gel or ointment) of SAP-I, and packaged as a moist wound dressing In some embodiments, a woven cloth product such as a gauze or other cloth product, is impregnated with a partially hydrated, semi-solid (gel) of SAP-I, pressed, dried, and packaged as a wound dressing. In some embodiments, a partially hydrated, semi-solid (gel) of SAP-I, is pressed into a sheet, dried, and packaged as a wound dressing. In some embodiments, a partially hydrated (gel) of SAP-I is packaged in a collapsable tube for direct topical application as an antimicrobial gel/ointment composition. In some embodiments, a partially hydrated (gel) of SAP-I is combined with a local anesthetic, such as lidocaine or benzocaine, for example, for use as a topical antimicrobial anesthetic.

In some embodiments, SAP-I particles are impregnated or coated onto a porous fabric, paper, or open-cell foam substrate to form an air filter. The filter may be flat, flat-pleated, or formed into a cylindrical packing filter element for insertion into an in-line cartridge filter. Elemental iodine is a volatile crystalline material at room temperature that sublimates into iodine vapor. Attaching large amounts of iodine within an SAPI-I reservoir allows for controlled release of iodine to disinfect air flowing through a filter element disposed within an air handler system of an interior commercial or residential space. In some embodiments, a disposable face mask or porous sheet insert, of woven or non-woven, is impregnated with SAP-I particles.

Investigation using a wicking, non-woven "tea bag" measuring about 2" by about 3" and containing about 0.75 grams of SAP-I showed the envelope material actively wicked water into the composition which slowly, according to intake, expanded into a soft pillow shape that did not release its contents under pressures generated by normal handling. Although the dried SAP-I powder composition may not be initially distributed evenly throughout the poultice, upon placement in the wound bed and upon hydration, the material expands and evenly disperses, completely filling out its constrainer. The loose, dry SAP-I powder allows the poultice to conform to the wound bed, whether the wound has a broad-based saucer-like shape; or the poultice dressing can be folded and packed into deep tunneling wounds. The fully hydrated pillow configuration provides a gently compressive cushioning non-adhering effect against the wound surface. If the envelope is made of strong nylon mesh, this kind of poultice would be ideal for military wound packing.

Moreover, absorption and wicking from the moist wound bed initiates release of iodine from the SAP-I. As the moisture content of the SAP-I composition increases, the fabric-encased dressing contents will expand to contact all surfaces of the wound. In some embodiments, the SAP-I composition is a SAP-I powder-coated dressing affixed to the wound bed using a conventional adhesive-bordered dressing tape to create an "island dressing" which may not require a secondary dressing.

When constrained beneath a lightly compressive adhesive, transparent, semi-occlusive film dressing sheet (i.e., Tegaderm®, manufactured by the 3M corporation, Maplewood, Minnesota), the expanding polymer-containing packets closely conform to and exert light pressure on the wound surface. This accomplishes at least four important functions:

(1) the SAP-I composition uniformly absorbs exudate fluid from all areas of the wound bed;

(2) an evenly distributed concentration of iodine is brought into direct contact with microorganisms colonizing the wound surface;

(3) light pressure generated by expansion of the composition constrained beneath the occlusive dressing has a hemostatic effect; and (4) iodine content can be monitored by direct visualization of the composition color through the clear semi-occlusive film without removing the dressing, wherein the composition color changes from blue-black to greyish white as the iodine is gradually dissipated through oxidation reactions with microbes and glycoproteins in the wound exudate.

In some embodiments, the encased dressing is combined with an inert incipient material to add bulk and further facilitate wound bed coverage, particularly when the dressing is initially applied prior to absorption of wound exudate. In some embodiments, a composition comprising a SAP-I backing sheet attached to a collagen or alginate sheet is manufactured as a thin biocidal composition dressing, having a thickness of about 3 millimeters ("mm") to about 5 mm. In some embodiments, the thin sheet has a thickness of about 5.1 mm to about 7 mm. In some embodiments, the thin sheet has a thickness of about 7.1 mm to about 10 mm. In some embodiments, the thin sheet has a thickness of greater than about 10 mm.

Polymeric iodophor composition wound dressing combinations described herein are versatile dressings which can be used to administer wound care in challenging or out-of-hospital settings where comprehensive healthcare resources are not available, such as in third world medicine or on the battlefield/field hospital, at sea, in remote terrestrial environments, and during space travel, for example. These absorbing thin sheet combinations may be cut and trimmed to any size, and then stacked to fill deeper areas of the wound bed and then overlain, if necessary, with a secondary dressing.

Dried SAP-I powders can be formed into poultices or topical powder used alone, or as salves, applied directly to the wound. In some embodiments, gel forms are produced from less cross-linked polymers resulting in useful iodophor gels/ointments/creams that can be easily applied to a wound by squeezing from a tube or spread with a tongue depressor, for example. This method of application is particularly useful for dressing a burn wound. The resulting non-adherent iodine depleted granular gel derived from a SAPI powder can be easily removed during a dressing change by flushing with sterile water or isotonic fluid similar to removal of cadexomer gel dressings known in the art. In some embodiments, the wound is left open to air following application of the gel. In some embodiments, the wound is covered with gauze. In some embodiments, the gel is added to a commercially available dressing material to confer antimicrobial properties. In some embodiments, the gels are used in place of conventional topical antibiotic ointments or powders, e.g., sulfanilamide, retapamulin, silver sulfadiazine, bacitracin, neomycin, polymyxin b, or other commonly used topical antibiotics, whether available over-the-counter or requiring a prescription. In some embodiment, a SAP-I gel composition is applied onto a hemostatic nasal packing sponge to prevent infection e.g., Merocel® nasal packings obtained from the Medtronic Corporation.

In some embodiments, gel compositions comprising SAP-I are applied to a substrate, dried, and packaged as a wound dressing. Substrates include non-woven materials, such as medical grade polyurethane open-cell foam, for example. These gel-based dressings conform to the wound bed upon contact with serous exudate, have extraordinary absorbent capacity as discussed herein. The dressings release iodophor derived iodine not only to the wound bed, but also to remove, non-viable tissue and proteinaceous exudate colonized with microorganisms. Non-viable tissue and proteinaceous exudates are potent environments for bacterial growth. SAP-I containing gels act as an active antimicrobial largely preventing antimicrobial growth in the absorbed exudate, and thereby preventing reinfection from colonized exudate to migrate back into the wound between dressing changes.

In some embodiments, a polyvinyl alcohol foam as described in U.S. Pat. No. 5,071,648 is particulated or combined with SAP-I of various ratios, compressed, and contained alone or in combination with other compositions for packing in flexible pouches which combination may modify iodine delivery rate. These pouches are placed into the wound, contacting and conforming to the wound bed as the composition progressively hydrates and expands with exudate fluid. In some embodiments, the composition is placed directly into deep wounds as a poultice.

In some embodiments used in non-wound care applications, the SAP-I powder is used as an antiseptic sanitizer and absorbent. Some non-limiting examples of non-wound care uses of the SAP-I powder material includes antimicrobial foot powders; also, for damp environments or surface treatments to prevent the growth of mold, mildew, or biofilms for moist conditions.

In some embodiments, the SAP-I composition is deposited onto an adhesive surfaced material making it an antimicrobial sheet. In some embodiments, the SAP-I composition is adjunct into a hemostatic dressing. In some embodiments, the SAP-I composition is incorporated into an island dressing as a band-aid type. In some embodiments, the SAP-I composition can be incorporated into other traditional, commercial dressing materials. In every one of these cases, SAP-I adds the antimicrobial capacity to these existing bandages.

In some embodiments, the SAP-I composition may be incorporated into a disposable feminine hygiene pad as odor control. In some embodiments, the SAP-I composition likewise may be incorporated into an adult diaper. Similarly, in some embodiments, the SAP-I composition is incorporated into other disposable articles where a super-absorbent antimicrobial substrate is desired to sanitize or deodorize.

For example, commercially available flat-sheet dressings are supplied in conventional dressing sizes; i.e., 4"×4" and others. These and larger sheet sizes can be cut and trimmed to any dimension or shape from SAP-I containing sheets suitable for use in a specific wound size. Smaller pieces may be cut and stacked to form layers from larger sheets to conveniently achieve increased thickness and regulate the amount of antimicrobial to focus on wound areas which may be deeper, or having increased amounts of bleeding, or generate larger amounts of exudative fluid.

In some embodiments, a partially hydrated paste of SAP-I is layered onto a nonabsorbent substrate (e.g., glass) and dried. The SAP-I is partially or fully dried, the substrate is removed leaving a sturdy black film of SAP-I material. The film is strong, continuous, and slightly elastic. When the film is applied to an open wound, the film swells and thickens as it hydrates and delivers the iodophor to the wound bed. As the amylose component of the SAP-I breaks down into a gel, iodine is released and treats the wound and absorbs the exudate, and progressively loses it black color. When no black or deep blue color remains, the gel—depleted of its iodine—is easily removed by flushing with sterile water or isotonic fluid.

Dressings in form of poultices and thin sheets comprising SAPI-I compositions are super-absorbent, retain absorbed fluid under pressure, have relatively low initial (dry) bulk, and excellent hydrophilic and wound bed releasing characteristics.

In some embodiments, a partially hydrated (gel/ointment) of SAP-I is combined with an anesthetic, such as lidocaine or benzocaine, for example, for use as a combination topical antimicrobial-anesthetic.

In some embodiments, SAP-I particles are impregnated into a porous fabric, paper, or open-cell foam substrate to form an air filter. The filter may be flat, flat-pleated, or formed into a cylindrical packing filter element for insertion into an in-line cartridge filter. Iodine sublimates to a vapor at room temperature. Complexing large percentages of iodine in an SAPI-I reservoir allows for controlled release of iodine to disinfect air flowing through a filter element disposed within an air handler system of an interior commercial or residential space.

In some embodiments, a reusable face mask, stain and odor free, made from fabric, woven or non-woven, impregnated with a SAP-I preparation, which is disposable when the color changes. In some embodiments, a sheet of SAP-I material is configured as a removable insert for a face mask or respirator that may be replaced with a fresh SAP-I insert when the iodine component has vaporized and dispersed. A color change of the insert from blue-black to gray-white indicates depletion of the iodine and replacement with a fresh insert is needed. In all air and breath sanitizing, as in wound care, color change is universally an indication of the need for replacement.

In some embodiments, a cotton-tipped applicator is impregnated with SAP-I composition for nasal swabbing for use as an antimicrobial barrier in the nasal cavity.

In some embodiments, dry SAP-I fine powder is used as an antibacterial, moisture-absorbing, deodorizing foot powder.

In some embodiments, a strip of cotton or synthetic material configured for insertion into the external auditory canal ("EAC") is impregnated with a SAP-I composition. Currently, the use of antibiotics in ear wicks in these applications may lead to emergence of drug resistant bacteria. In contrast, iodophor drug resistance is unknown. In this and some other embodiments, the SAP-I composition may be used to treat external otitis from bacterial or fungal infection ("swimmer's ear"). The EAC dressing may be particularly effective because with hydration, the SAP-I swells to provide controlled release topical iodine therapy to all surfaces of the EAC and prevents the dressing from being easily dislodged from the ear canal.

In some embodiments, an SAP-I film insert is applied to a skin-contacting surface of a transdermal drug delivery device, such as a patch pump used to deliver insulin or other drugs.

FIG. 1 is an illustration depicting a method of forming a wound dressing containing a polymeric iodophor composition. FIG. 1 shows a mixing step 110, a drying step 120, a hydrating step 130, a permeating step 140, and a packaging step 150.

In some embodiments, mixing step 110 comprises mixing a dry starch-acrylic polymer with elemental dry, powdered iodine under moist conditions to form an SAP-I. Examples of dry starch-acrylic polymers include commercially available products comprising an amylose-based starch complexed with an acrylic polymer. Non-exclusive examples of these products include SGP 502S polymer (Henkel Consumer Goods, Stamford, CT), IM and MPS series Sanwet polyacrylate starch grafts (Sanyo Chemical, Kyoto, Japan). Dextran-polymer derivatives by Ethicon (Ethicon US LLC, Cincinnati, OH), and B 204 polymer (S&I Solutions Company, Seoul, Republic of Korea). Upon completion of mixing under moist conditions, the SAP-I forms curds.

To form an SAP-I comprising twenty percent (20%) iodine by weight, mix 2 parts elemental iodine crystals with 8 parts of the starch-acrylic polymer. Mixing is accomplished by grinding the materials together to form a fine, homogeneous powder, such as with a mortar and pestle or a pharmaceutical-grade grinding or milling machine known to those of skill in the drug manufacturing arts.

In some embodiments, drying step 120 comprises drying the SAP-I at a temperature not greater than 125 degrees Fahrenheit. This is done, for example, in a drying oven at a set temperature between about 110 and about 120 degrees Fahrenheit, in some embodiments. In some embodiments, the drying oven is fitted with an iodine vapor capturing device for neutralizing any free iodine that may escape e.g., a thiosulphate air filtering cartridge. In some embodiments, drying step 120 additionally comprises grinding the dried CAP-I curds into a powder.

In some embodiments, hydrating step 130 comprises hydrating the dried SAP-I to form a gel or an ointment. A quantity of greater than about eighty (80) times the weight of the SAP-I powder is mixed vigorously with water forming a gel. More or less water is used as needed to achieve the designed consistency necessary to facilitate permeating the dressing material in permeating step 130 below. This may vary depending on the type of dressing material or consistency of the gel or the ointment used, in some embodiments.

In some embodiments, permeating step 140 comprises spreading the SAP-I gel onto a dressing material to coat the dressing material with the gel or the ointment. In some embodiments this is done by rolling under some pressure the SAP-I gel between cylinders onto a substrate. In some embodiments, the dressing material coated with the SAP-I gel or ointment is dried by repeating drying step 120.

In some embodiments, packaging step 150 comprises packaging the dressing in a moisture-proof, vapor-proof packaging. In some embodiments, the package material is a commercially available mylar polyethylene foil. In some embodiments, the packaging is a commercially available, peelable mylar package, with or without a foil layer. In some embodiments, the SAP-I dressing comprises a fully dried SAP-I component. SAP-I dressings are compatible with electron beam sterilization methods.

ADDITIONAL EXAMPLES

Example #1—Raw Materials

Some examples of commercially available grafted starch super-absorbent polymer compositions of varying solubility comprising amylose to complex with iodine combinations for forming SAP-I iodophors include:

SGP 502S polymer (Henkel Consumer Goods, Stamford, CT)

IM and MPS series Sanwet polyacrylate starch grafts (Sanyo Chemical, Kyoto, Japan)

Dextran derivatives by Ethicon (Ethicon US LLC, Cincinnati, OH)

B 204 polymer (S&I Solutions Company, Seoul, Republic of Korea)

Iodine ACS grade Iodotek Company

Example #2—SAP Bulking Components

These materials do not contain amylose thus do not combine with iodine. These polymers are in the class of cellulose homopolymers or neutralized cross-linked acrylics with no starch component, e.g. polyolefin particles. They are used to increase bulk, for better distribution of the SAP-I composition across a wound bed. These agents include:

Kimberly Clark pulp graft polymer (Kimberly-Clark Corporation, Irving, TX The AmeriChem Company (Suppliers of polyolefin filler)

Sanfresh ST series (Sanyo Chemical, Kyoto, Japan)

Example #3—Hemostatic Agents

These materials may be added to any dressing or poultice and include:

oxidized or epoxidized cellulose from Ethicon (Ethicon US LLC, Cincinnati, OH)

collagen and/or alginate powders fibrinogen chitin

BloodSTOP® styptics compatible biologicals and pharmacologics

Example #4—Method of Manufacture of SAP-I Powders

Mix 2 grams of pure elemental iodine crystals and 8 grams of super-absorbent carboxylate salt of a polyacrylonitrile graft co-polymer (SAP) of starch by grinding, such as in a mortar and pestle, for example. Grind mix thoroughly into a fine powder, assuring that the iodine powder is homogeneously blended with the superabsorbent polymer powder. Add the mix to a high shear mixer processor. Blend at medium speed.

The tan super-absorbent polymer/iodine mix (SAP-I) continuously darkens from a cinnamon color to dark brown as moisture is slowly added, and finally to black. The reaction rate is dependent on the rate of the introduction of water, which carries the iodine to combine with the polymer without any of the polymer forming lumps that exceed the size of curds which can then be easily dried and then ground into powder. The water is added to the mix only at a rate which maintains enough dampness to continually transfer the iodine from its low water solubility state.

Dry the resultant damp curd at 110° F. until the weight is constant and the material is friable enough to be mechanically ground to a flake/powder that will pass through selective sieve openings. This results in a SAP-I powder or flake form (depending on the kind of grinding and sieve size) containing about 20% iodine by weight, in some embodiments.

The more insoluble grades of SAP-I powder are capable of absorbing at least 80 times its weight with water, and when fully saturated, becomes an easily flushable, non-sticky, granular gel. Full saturation of the SAP with iodine is confirmed by adding the powder or flakes to an excess amount of water and noting whether an orange tinted supernatant appears above the black gel precipitant. An orange color in the supernatant indicates the presence of unreacted free iodine. If the supernatant is a blue-green color, it indicates that the elemental iodine has been substantially combined. A blue-colored effluent is characteristic of the SAP-I iodophor. The iodine content of the SAP-I iodophor powders or flakes is adjustable. Particle size is configured to match the intended application, e.g., a medium grind for a poultice or a finer powder to spread directly onto a wound bed for burn treatment, or a super-fine particle size for use as a coating or foot powder, or for blending with other components, e.g., coagulant containing poultices.

In some embodiments, the SAP-I powders alone or mixed compositions are configured for packaging by commercial teabag manufacturing machines that measure, fill, seal, and label the bag.

Example #5—Poultice Dressing

In some embodiments, a poultice envelope dressing is made using high wet-strength retentive tea bag-like heat sealable paper (e.g., made by Gladfelter Tea Paper Company, Charlotte NC) or a heat-sealable porous woven cloth, or (ideally) a hydrophilic, wicking, high tensile-strength, polyester-based heat-sealable non-woven web. Typically, a 4"×3" envelope contains about 1.0 grams of SAP-I powder/flakes, in some embodiments. Upon hydration, the envelope swells to absorb about one ounce (1 oz.) of fluid thus forming a strong, soft pillow-like dressing, delivering controlled amounts of microbicidal iodine to a wound site and absorbing exudate. These fully saturated pillows do not lose mechanical integrity or leak absorbed exudate under normal handling pressure. A poultice envelope of approximately the same dimensions (but containing additional SAP-I to absorb excessive exudate or to increase intervals between changes), may be formed using a pleated or gusseted envelope. To obtain a thinner, less firm pillow dressing, a smaller amount of SAP-I powder is used.

Example #6—Island Dressing

In some embodiments, SAP-I powder is centered on an adhesive-coated dressing tape by spreading and pressing the powder to the adhesive and then layering with a thin hydrophilic porous web e.g., envelope material, to prevent any particle migration, if required. A surrounding adhesive margin is left uncoated for adherence to intact skin surrounding the wound. Placing the dressing over the wound and pressing around the adhesive border seals the dressing to the skin, forming a pouch containing SAP-I over the wound. The tape ends can be extended to produce adhering tails for better attachment.

Example #7—Multifunctional Healing Poultice

Blend in a 1 to 1 ratio 20% Sap-I particles and a hemostatic agent, such as oxidized cellulose (Ethicon US LLC, Cincinnati, OH), oxidized cellulose fibers, collagen, chitosan, BloodSTOP, VetiGel, or styptic salts of iron or aluminum. The resulting powders or flake combinations have antimicrobial, super-absorbent and hemostatic properties, and useful healing aids especially useful for military and first aid.

Example #8—Personal Absorbent Devices

Blend Kendall Company's fibrous super-absorbent homopolymer (absorbent filler) or the like with SAP-I (20% iodine) powder to add antimicrobial effectiveness, more absorption and odor control for personal hygiene and other adult diaper liquid absorption products.

Example #9—Topical SAP-I Antimicrobial Ointment

In a mixer, blend ten (10) grams of SAP-I (20% iodine) of any of the more soluble, less cross-linked starch-grafted sodium polyacrylate grades or of the more saponified poly-acrylate mix types, e.g., Sanyo Company's MPS series polymers. Add the powder mix slowly to a processor containing 200 cc's of water during vigorous mixing until a smooth black gel is obtained containing about 1% iodine.

This gel is suitable for application directly onto the wound site by delivery with a squeezable tube. Upon application to the wound, the gel begins the healing process, turning from black to an off-white gel thickened with exudate, indicating the iodine content has dissipated. Spent ointment is removed from the wound site by conventional irrigation procedures. This gel is useful as an initial dressing gel by itself, e.g., under a Band-Aid, or as an ointment applied to any other conventional bandage to improve its antimicrobial, longer term effectiveness.

To prevent drying out of these gel dressings, the dressing should be covered with a moisture-retaining secondary layer, such as Opsite® (Smith & Nephew, Inc., Memphis, Tennessee) or Tegaderm® (3M corporation, Maplewood, Minnesota), for example.

Example #10—Paper-Based Dressings

Apply the gel of the previous example to absorbent, thicker, wet strength paper (e.g., paper toweling) to uniformly coat the paper on one or both sides. Dry the coated sheet using a conventional drying oven at a temperature not exceeding 125° F. The flexible coated papers may be used as sheet dressings singly or layered to increase absorbency and iodine content. These inexpensive, antimicrobial, extra-absorptive papers may be made into continuous rolls and used for, et al., first aid, wound care, wiping and sanitizing applications. These antimicrobial, absorbent papers are especially useful for superficial wounds, island dressings, and for wrapping. When coated on paper toweling, the SAP-I treated product may be used as an absorbent, soft, sanitizing moisture removal/personal hygiene wipe, or as a sanitizing wipe for initial cleaning, or as a sanitizing wrap for medical and diagnostic instruments.

Example #11—Wet Dressing

Example #10 above is duplicated but used in the wet state by application to a conventional bandage substrate material such as cotton gauze or non-woven bandaging onto which the SAP-I ointment is applied. This impregnated pre-moistened dressing can be applied directly to the wound as a moist, antiseptic gel with a secondary moisture barrier dressing.

Example #12—Antiseptic Bandage Roll

A super-absorbent urethane foam continuous antimicrobial roll bandage or alternatively made of woven or non-woven, highly porous dressing material, elastic or non-elastic, is impregnated as in Example #10 then dried on the belt of a continuous dryer. This process deposits adherent SAP-I particles uniformly throughout to the substrate material, increasing absorbency and adding antimicrobial properties. These bandages, depending on the substrate, form a flexible, super-absorbent, antimicrobial, conformable, and mechanically protective light-weight dressing, especially suitable for battlefield roll-type bandaging and homeostasis. The roll-type SAP-I dressing may be dispensed like paper towels, is intrinsically sterile, and may be especially useful for field first aid and by third-world clinics.

When impregnated onto an elastic cloth and dried, e.g., an Ace-type bandage, the SAP-I forms discrete dry particles within the bandage's interstitial spaces and do not inhibit the stretching or porosity of the bandage. These dressing rolls in the form of elastic wraps are useful for simultaneously achieving compression, hemostasis, absorption, and antiseptic properties.

Example #13—To Make Consumer Strip Dressings

Any sheet from examples disclosed herein can be made into an antimicrobial island dressing trimmed to any size or shape by attaching the flat dressing to a self-adhering tape with extended wings with borders coated only with adhesive. Making a band-aid type transparent strip dressing using e.g., Transpore Tape (3M corporation, Maplewood, Minnesota), allows the observation of the color of the iodophor change from black to grey indicating the depletion of the iodine content indicating when replacement is needed.

Example #14—Tea Bag Poultices

A 4"×3" tea bag-type pouch envelope containing about 1.0 gram of SAP-I (20% iodine) is moistened and taped to the skin, producing a patch that delivers controlled release iodine over an extended period.

Example #15—Antimicrobial Face Masks

Masks can be made antimicrobial by coating with a SAP-I type gel or by adding a coated, removable SAPI-I insert. In some embodiments, the mask incorporates SAP-I foams or sheet strips interlayered with the construction of conventional face masks. The resulting antimicrobial face masks, either with coating or inserts, are comfortable and capable of sanitizing outgoing breath and incoming air, especially suitable for surgical and consumer masks and generally to filter environmental pollutants. The SAP-I does not have the staining or odor properties of conventional iodine preparations.

Example #16—To Sanitize the Air Environment

Antimicrobial porous media incorporating SAP-I compositions derived from the previous examples is packed into columns or formed into flat pleated filters to sanitize air in the presence of natural humidity or by moist injection. These rechargeable devices will show by change of color the depletion of the iodine content and the need for replacement, for medical, industrial and consumer air conditioners.

Example #17—Antimicrobial Wet Dressing

Coat onto the surface or permeate a skived sheet of medical-grade open cell hydrophilic foam e.g., 90-pore urethane\1⁄16th" to 1⁄4" thick, a SAP-I gel as described herein above is especially useful for burns, as it is a very soft, conformable and elastic dressing to follow the contours of the burn and absorbs exudate. The 20-pore very open foam sponge is permeated and dried to form a SAP-I sponge matrix to absorb exudate, and for negative pressure treatment (NPT). The larger porosity allows the passage of air removal during NPT.

Example #18—Black Films as Biocidal Barriers

A 1⁄16th inch or thicker layer of a more soluble grade e.g., MPS 1000 based SAP-I gel, is deposited on an acrylic plate and dried at 110 F. The resultant film is stripped off the plate and stored between layers of polyethylene film to prevent sticking. These black films are biocidal barriers that swell with moisture and are useful for treating for example, larger burn areas. The films are slightly elastic and relatively strong, and flushable.

Example #19—SAP-I Ear Wick

An absorbent iodophor ear wick is made by cutting an approximately ¾-inch square of SAP-I coated paper or foam rolled into tubes to be inserted into the ear canal to treat otitis externa. When hydrated with water of pH less than about 6.0, it will swell into a tubular gelatinous-surfaced wick, firmly fitting into the ear canal to treat the infection. The gelled surface prevents sticking to the ear canal wall while still preventing dislodgement and aids in release.

Example #20—Urethane Foam Sheet Dressing

Polyurethane open cell foam sheets of reticulated polyether or polyester, ⅛th to 3/16th inch thick having pore sizes of 20-90 pores per inch are impregnated with SAP-I gel formed as described herein above of various dilutions and iodine concentrations, and then dried. These dried foam dressings demonstrate good flexibility, adjustable iodine content as required, extraordinary absorbency, breathability, non-adherence to tissue, mechanical integrity, and changes color to indicate depletion of iodine and need for replacement. The foam protects the wound against mechanical impact due to its open-cell, resilient structure and because of its porosity, is suitable for negative-pressure therapy.

Example #21—Liquid Penetration and Detergency

Addition of a non-ionic wetting agent, such as Polaxamer 188 or similar types of surfactants, adds functionality to dissolve cleanse, remove, or penetrate biofilms, aid debridement, and improve wicking of the poultice envelope. Such agents can also be added to facilitate penetration of wound exudate into the poultice. The wetting agent in dry form is added to SAP-I powder at a 2%-4% concentration by weight. Alternatively, the wetting agent solution is sprayed and dried onto the finished poultice-envelope material.

A class of compositions comprising starch-acrylic polymers combined with elemental iodine has been disclosed. The SAP-I compositions release non-toxic amounts of iodophor iodine in a sustained, controlled manner. This makes these compositions particularly suitable for use in the care of open wounds chronically colonized with potentially invasive, infectious bacterial and fungal microorganisms. The absorptive and other physical properties of SAP-I compositions are ideally suited for incorporation on or with a variety of other materials to disinfect, remove exudate and provide a gently compressive dressing, and other functions.

The embodiments and examples set forth herein were presented in order to best explain the present invention and its practical application, and to thereby enable those of ordinary skill in the art to make and use the invention. However, those of ordinary skill in the art will recognize that the foregoing description and examples have been presented for the purpose of illustration and example. The description as set forth is not intended to be exhaustive or to limit the invention to the precise form disclosed. Many modifications and variations are possible, in light of the teachings herein above.

What is claimed is:

1. An antimicrobial composition comprising elemental iodine combined with a starch-polyacrylic graft copolymer to form a dry composition having a starch acrylic polymer-iodine complex, wherein the dry composition comprises elemental iodine at a concentration between twenty percent (20%) and twenty-five percent (25%) by weight, and wherein the dry composition is able to absorb at least eighty (80) times its weight in water.

2. The antimicrobial composition of claim 1, wherein the antimicrobial composition is formed as a powder.

3. The antimicrobial composition of claim 1, wherein the antimicrobial composition is formed as a flake.

4. The antimicrobial composition of claim 1, wherein the antimicrobial composition is formed as a gel.

5. The antimicrobial composition of claim 1, wherein the antimicrobial composition is formed as a sheet.

6. The antimicrobial composition of claim 1, further comprising a hemostatic agent.

7. The antimicrobial composition of claim 1, further comprising a bulking agent.

8. A wound dressing comprising: an iodophor formed from elemental iodine adducted to a starch-polyacrylic graft copolymer to form a dry composition having a starch acrylic polymer-iodine complex; and a bandage, wherein the starch acrylic polymer-iodine complex comprises elemental iodine at a concentration between twenty percent (20%) and twenty-five percent (25%) by weight, and wherein the dry composition is able to absorb at least eighty (80) times its weight in water.

9. The wound dressing of claim 8, wherein the iodophor is formed as a powder or a flake.

10. The wound dressing of claim 9, wherein the iodophor is incorporated into a poultice.

11. The wound dressing of claim 8, wherein the iodophor is incorporated into a coated foam.

12. The wound dressing claim 8, wherein the iodophor is incorporated into a gel.

13. The wound dressing of claim 8, wherein the iodophor is formed as a sheet.

14. The wound dressing of claim 8, further comprising a hemostatic agent.

15. The wound dressing of claim 8, wherein the bandage is an adhesive bandage.

16. The wound dressing of claim 8, wherein the bandage is a bandage roll.

* * * * *